(12) United States Patent
Ziegler

(10) Patent No.: US 7,771,659 B2
(45) Date of Patent: Aug. 10, 2010

(54) ARRANGEMENT AND METHOD FOR THE ANALYSIS OF BODY FLUIDS

(75) Inventor: Michael Ziegler, Schwaikheim (DE)

(73) Assignee: PVT Probenverteiltechnik GmbH, Waiblingen (DE)

(*) Notice: Subject to any disclaimer, the term of this patent is extended or adjusted under 35 U.S.C. 154(b) by 521 days.

(21) Appl. No.: 10/502,130

(22) PCT Filed: Jan. 11, 2003

(86) PCT No.: PCT/EP03/00200
§ 371 (c)(1),
(2), (4) Date: Aug. 19, 2005

(87) PCT Pub. No.: WO03/060484
PCT Pub. Date: Jul. 24, 2003

(65) Prior Publication Data
US 2006/0014295 A1 Jan. 19, 2006

(30) Foreign Application Priority Data
Jan. 19, 2002 (DE) ............... 102 05 772
Jan. 19, 2002 (DE) ............... 102 05 773
Apr. 26, 2002 (DE) ............... 102 18 692
Apr. 26, 2002 (DE) ............... 102 18 693

(51) Int. Cl.
*G01N 35/00* (2006.01)
*G01N 15/05* (2006.01)
*G01N 33/49* (2006.01)

(52) U.S. Cl. .......... 422/82.05; 422/63; 422/65; 422/100; 436/164; 356/39; 356/246; 356/441; 356/442

(58) Field of Classification Search ............ 422/63, 422/65, 67, 100, 72; 436/180
See application file for complete search history.

(56) References Cited

U.S. PATENT DOCUMENTS

| 4,710,874 A | 12/1987 | Cinqualbre |
| 5,003,488 A | 3/1991 | Hardy |
| 5,012,116 A * | 4/1991 | Russell .......... 250/559.46 |

(Continued)

FOREIGN PATENT DOCUMENTS

DE 35 20 962 A1 12/1985

(Continued)

OTHER PUBLICATIONS

Sumitomo Metal Ind Ltd, "Detecting Device for Seamed Part of Electro-Resistance Welded Pipe and Its Method," Patent Abstracts of Japan, vol. 1998, No. 11, Sep. 30, 1998.

(Continued)

*Primary Examiner*—P. Kathryn Wright
(74) *Attorney, Agent, or Firm*—Kriegsman & Kriegsman (57) ABSTRACT

The invention relates to an arrangement and a method for the analysis of body fluids (21), whereby an image recording device (30) is arranged in a low-reflection, preferably zero-reflection chamber (16), provided with an illumination device (45) and connected to an electronic image analyzer. The image recording device (30) is focused on a container (20), containing the body fluid (21) in an analysis position (22), in order to take at least one image of the body fluid (21), analyzed by means of an image analysis software which determines the quality of the body fluid (21).

14 Claims, 6 Drawing Sheets

U.S. PATENT DOCUMENTS

| | | | |
|---|---|---|---|
| 5,308,506 A | * | 5/1994 | McEwen et al. ............ 210/745 |
| 5,365,343 A | | 11/1994 | Knapp |
| 5,617,204 A | | 4/1997 | Hinata |
| 5,719,679 A | * | 2/1998 | Shimizu et al. ............ 356/428 |
| 5,763,265 A | | 6/1998 | Itsuzaki et al. |
| 5,835,620 A | * | 11/1998 | Kaplan et al. ............... 382/133 |
| 6,139,800 A | * | 10/2000 | Chandler ................. 422/82.08 |
| 6,599,476 B1 | * | 7/2003 | Watson et al. ................. 422/63 |

FOREIGN PATENT DOCUMENTS

| | | |
|---|---|---|
| DE | 41 09 118 A1 | 9/1992 |
| DE | 296 08 120 U1 | 8/1996 |
| DE | 197 42 160 A1 | 4/1998 |
| DE | 695 18 834 T2 | 1/2001 |
| EP | 0 342 730 A2 | 11/1989 |
| EP | 0422845 A2 | 4/1991 |
| EP | 0 637 744 B1 | 11/2001 |
| JP | 09133687 * | 11/1995 |
| WO | WO 96/39618 A1 | 12/1996 |
| WO | WO 99/28724 * | 6/1999 |
| WO | WO 01/23864 A1 | 4/2001 |

OTHER PUBLICATIONS

Fuji Electric Co Ltd, "Method for Inspecting Inside of Container," Patent Abstracts of Japan, vol. 016, No. 003 (P-1294), Jan. 7, 1992.

Sony Corp., "Picture Tube Assembly Inspection," Patent Abstracts of Japan, vol. 1996, No. 04, Apr. 30, 1996.

Meiji Denki Kogyo KK, "Instrument for Measuring Quantity of Serum in Blood-Collecting Test Tube," Patent Abstracts of Japan, vol. 1997, No. 09, Sep. 30, 1997.

Hitachi Ltd, "Instrument and Method for Measuring Serum Quantity," Patent Abstracts of Japan, vol. 2000, No. 23, Feb. 10, 2001.

* cited by examiner

ARRANGEMENT AND METHOD FOR THE ANALYSIS OF BODY FLUIDS

BACKGROUND OF THE INVENTION

The invention relates to an arrangement and to a method for analyzing body fluids.

Before body fluid, such as blood serum or blood plasma, is analyzed, centrifuged samples of body fluid are examined as to whether they are "good", that is to say suitable for analysis, or whether they are discolored or cloudy because of contaminants or specific clinical pictures. This is the case, for example, when so called clots (conglomerations of solid components) are contained in the blood sample, or when the blood samples are hemolytic, lipemic or icteric. The detection is currently performed manually by visual inspection of the samples before the latter are further processed. This mode of procedure is time consuming and labor intensive and leads to errors in subsequent laboratory operation, and is attended by downtimes for analytic equipment and by time consuming reworking.

SUMMARY OF THE INVENTION

It is the object of the invention to create an arrangement with the aid of which the quality of the body fluid to be analyzed and its quantity can be reliably determined.

This is achieved according to the invention by providing an image recording device for determining the quality and the quantity of the body fluid and connecting it to an electronic image evaluation apparatus. The image recording device records an image of the body fluid to be analyzed. This image is evaluated by the image evaluation apparatus. A reliable, quick and automatic determination by machine of the quality and quantity of the body fluid to be analyzed is thereby possible. The apparatus according to the invention and the method according to the invention permit a substantial automation and rationalization of the analysis of blood samples, and thus a substantial saving in time and cost.

Advantageous developments follow from the subclaims. The image recording device can be, for example, a photographic still camera, a color image camera, a video camera or a spectral camera. Other optical devices can, of course, also be used for recording images or image files.

A particular advantageous development provides that the arrangement according to the invention is designed such that the body fluid is provided in a chamber with few optical reflections and, if possible, in a chamber with no optical reflections, said chamber being in a container, and that the image recording device is aligned with and focused on the container, which is in an analysis position. It is thereby possible to achieve recordings that are of particularly good quality, and so the automatic image evaluation is affected by error to the least possible extent.

In this case, in its vertical alignment, the image recording device can be aligned with and focused on the container at an acute angle. It is possible in this way to avoid at least partially optical reflections that could falsify the result of analysis, and so it is possible to obtain an image of the body fluid that is as unfalsified and informative as possible.

This aim can be supported by an illuminating device provided in the chamber—preferably with no optical reflections—for the purpose of illuminating the container containing the body fluid with as few reflections as possible. A number of refinements are conceivable here alternatively or cumulatively. Firstly, the illuminating device can preferably be arranged above the container, and this leads to a reduction in the reflection via empirical trials. The arrangement and design of the illuminating device can also, for example, be provided such that arranged in each case on both sides of the container located in the analysis position is a lateral lamp, the arrangement being such that the mid points of the two lamps and the mid point of the container lie on a straight line (A), and that a further, middle lamp is provided and arranged in such a way that the mid points of this middle lamp and of the container likewise lie on a straight line (B), which runs perpendicular to the line (A). Furthermore, the lamps can be arranged such that they each have the same spacing from the container. This spacing can be, for example, sixty [60] millimeters in a concrete exemplary embodiment. Finally, the vertical height of the lateral lamps arranged on both sides of the container located in the analysis position can be of greater dimension than the vertical height of the middle lamp. In the concrete exemplary embodiment, the difference in height between the two lateral lamps and the middle lamp can be, for example, sixteen [16] millimeters. In a further embodiment, a scanner can be provided that is aligned with the container located in the analysis position. This scanner is preferably a bar code scanner and advantageously permits the edges of a label located on the container to be detected. The bar code on the label is read at the same time, thus permitting the sample to be uniquely identified. The container can thereby subsequently be brought into an analysis position in a particularly simple way by means of control software that controls the movement, for example, of a lifting rotary gripper, in which position the label is situated on the side of the container averted from the image recording device.

In addition, in order to mask out the bar code it is possible to provide an antireflection plate that is arranged on the side of the container turned away from the image recording device. In this case, the antireflection plate is preferably provided with a white surface and can have a concave depression adapted to the peripheral shape of the container, in order to adapt the contour to that of the container and to mask out the bar code as completely as possible. In this way, the images of the body fluid recorded by the image recording device are, in a particularly advantageous way, incapable of being falsified by the bar code, since the bar code is masked out by the antireflection plate. If appropriate, in order to avoid additional reflections, the depression can merge with the aid of rounded-off portions into in each case a flat surface of the antireflection plate, and the surfaces can end in each case in a sharp-edged vertical edge that serve as measuring edges.

The container is preferably moved by means of a lifting rotary gripper. In order to create space therefor, the antireflection plate is arranged such that it can be moved away from the container from a position bearing against the container in the direction of the optical axis of the image recording device, and such that it can be moved up to the container again. The handling apparatus itself, that is to say, for example, the lifting rotary gripper, is provided for conveying a container from a transport position into its analysis position. Depending on the arrangement of the label, the handling apparatus rotates the container into a position in which the image recording device can produce a correct image of the body fluid located in the container.

In this case, the image recording device can produce at least one image of the body fluid that is analyzed by means of image processing software. Depending on what is required, one or more detailed images are produced that are combined to form an overall image by means of the image processing software.

The further features and advantages are to be gathered from the description of an exemplary embodiment of the invention illustrated in the following drawings and from the further subclaims. In the drawings:

Figures 1, 2, 7, 8:
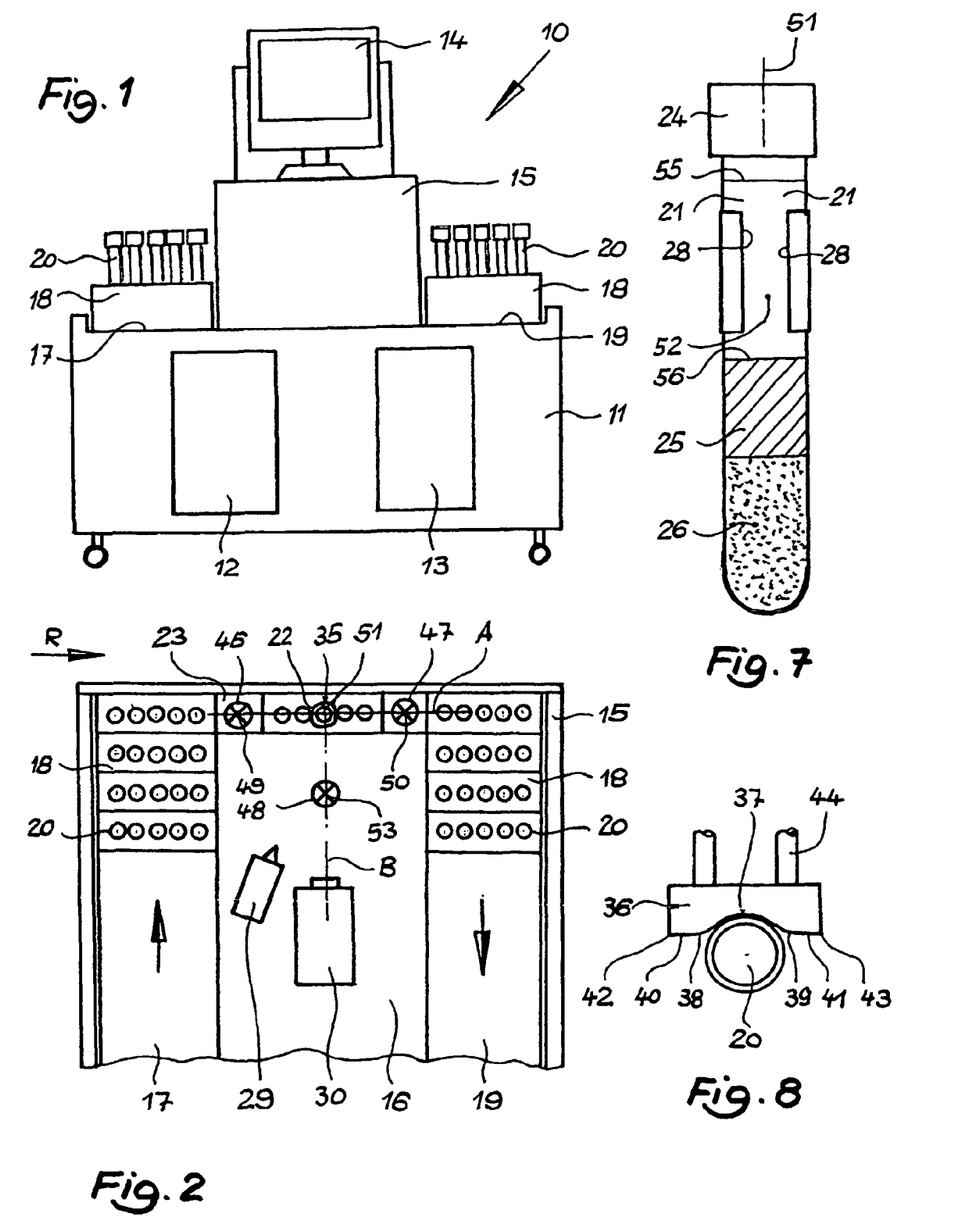
FIG. 1 shows the analysis device according to the invention in a front view, in a schematic illustration that is not true to scale.
FIG. 2 shows the arrangement according to the invention for analyzing body fluid, in a plan view in a schematic illustration that is not true to scale.
FIG. 7 shows a container used with the arrangement according to the invention.
FIG. 8 shows an illustration of a detail of an antireflection plate in plan view, in a schematic illustration that is not true to scale.

FIG. 1 illustrates the whole of a device 10 for analyzing body fluid. In essence, the device 10 comprises a cabinet 11 for holding a control computer 12 operated by control software, and for holding an image processing computer 13 operated by image processing software. The data determined by the computers 12 and 13 are displayed on a computer display screen 14. Arranged on the cabinet 11 is a housing 15 that surrounds a chamber 16 with no optical reflections.

A transport track 17 for feeding into the housing 15 containers 20 containing body fluid 21 located in racks 18 is provided on one side of the housing 15. On the side of the housing 15 opposite the transport track 17, a transport track 19 is provided for carrying off containers 20 with analyzed body fluid 21. The body fluid 21 to be analyzed can be blood serum, blood plasma or the like.

FIG. 2 shows a plan view of the open housing 15. The transport tracks 17 and 19 are connected to one another by a transversely running transport track 23. The containers 20 located in the racks 18 are brought one after another into an analysis position 22 on the transport track 23.

The analysis position is fed containers 20 with centrifuged body fluid 21 such that, as illustrated in FIG. 7, the body fluid 21, for example blood serum, is located in the upper region of the container 20, a separating means 25 is located in the middle region, and a blood clot 26 is located in the lower region. The container 20 is sealed with a cap 24. Affixed in the region of the body fluid 21 is a label 27 whose mutually opposite end edges 28 have a mutual spacing of at least 6.5 millimeters that permits a window 52 for a free view of the body fluid 21.

The chamber 16, which has few and, if possible, no optical reflections is equipped, for example, with inner walls having matte black surfaces. An image recording device 30 and a scanner 29 are accommodated in the chamber 16, which has few and, if possible, no optical reflections, the image recording device 30 being aligned with and focused on the container 20 containing the body fluid 21, while the scanner 29 is aligned with and focused on the label 27.

Figure 3:
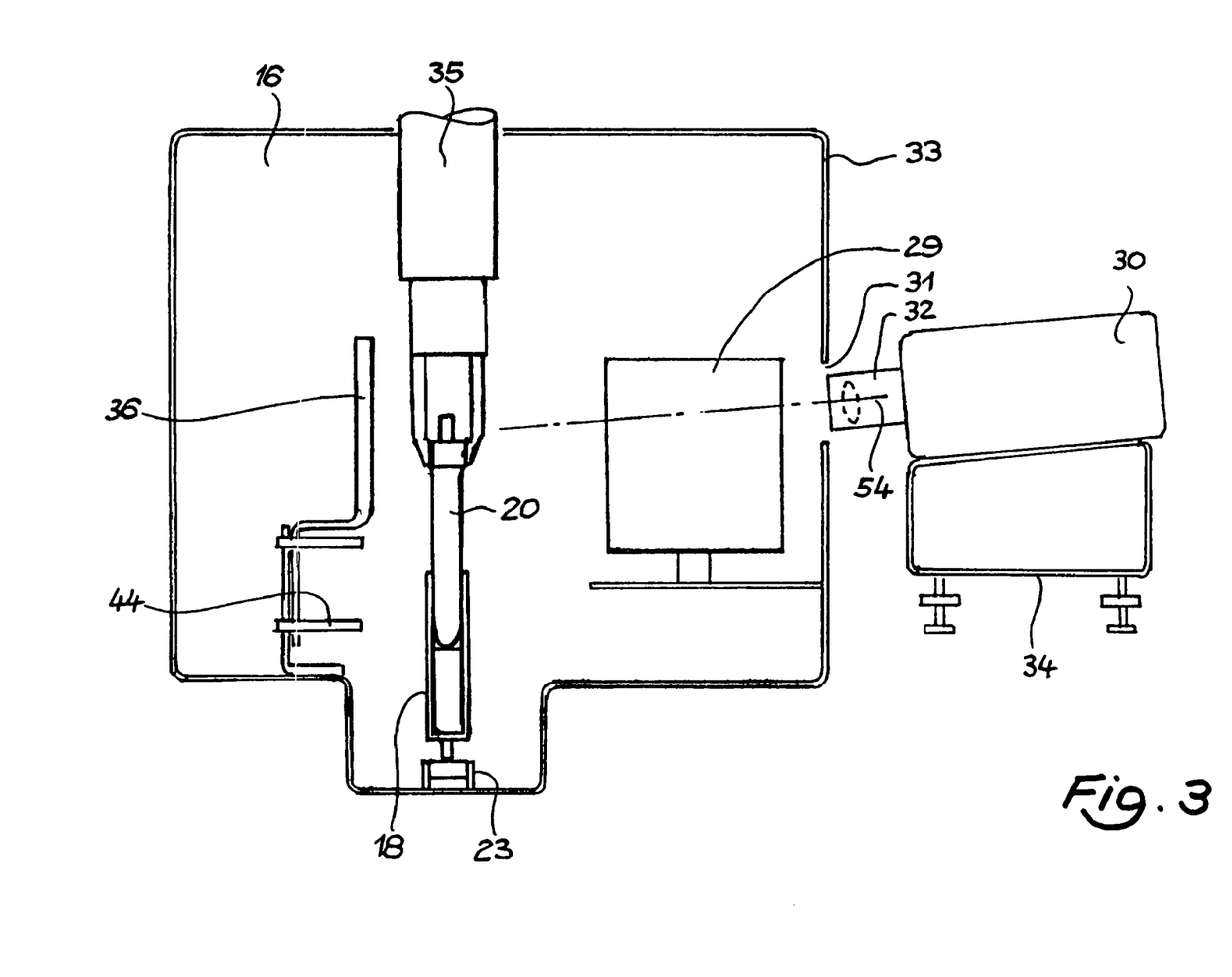
FIG. 3 shows the arrangement in accordance with FIG. 2 in the direction of view R with a container located in the transport position, in a schematic illustration that is not true to scale.
Figure 4:
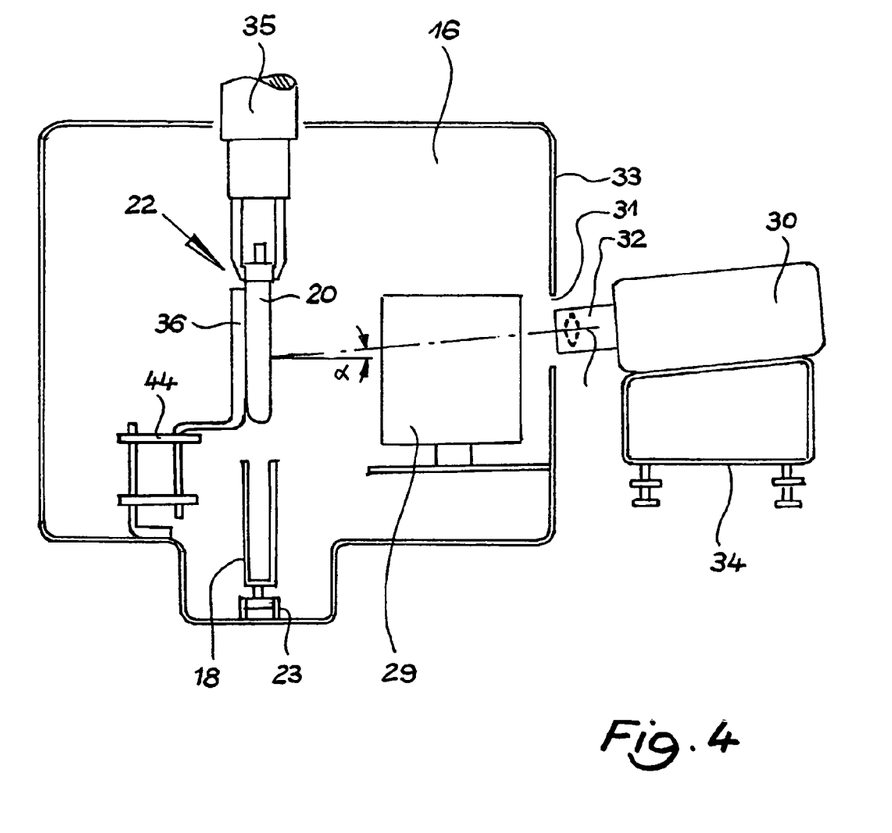
FIG. 4 shows the arrangement in accordance with FIG. 2 in the direction of view R with a container located in the analysis position, in a schematic illustration that is not true to scale.
Figure 5:
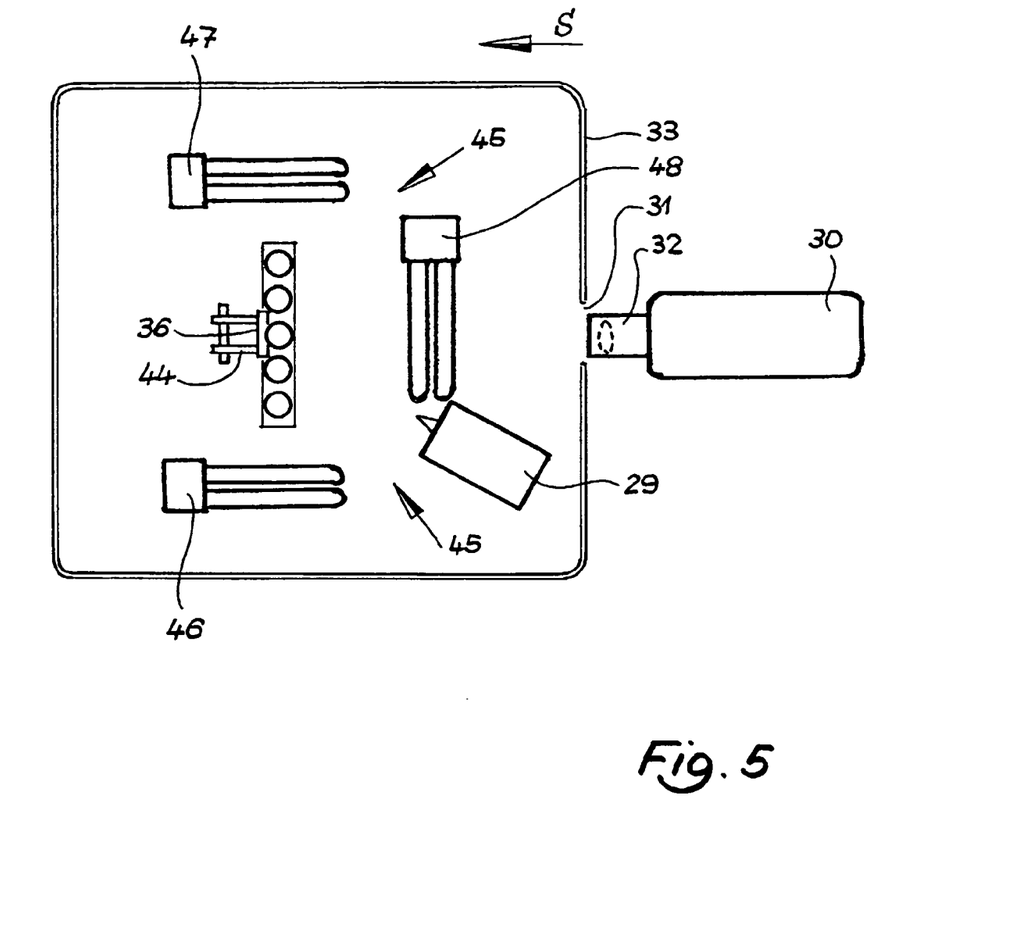
FIG. 5 shows the arrangement in accordance with FIG. 2 with an illuminating device in a plan view, in a schematic illustration that is not true to scale.

The image recording device 30 can also be arranged outside the chamber 16, although then a lightproof opening 31 for the passage of the objective 32 of the image recording device 30 is formed in a wall 33 of the chamber 16 (as shown in FIGS. 3, 4 and 5). The image recording device 30 can be a still camera, a color image camera, a video camera, a spectral camera or the like. A color image camera, for example a 3CCD video camera, is preferred. Depending on the geometry of the arrangement according to the invention, the settings of the color camera, such as focusing, white balance, diaphragm setting, filling-in, can be permanently preset. However, they can also be readjusted with the aid of the image evaluation software when the data reported by the image evaluation software to the control software (see further below on this point) are of reduced quality with reference to the reference data stored in the computer 13. The connection between the image recording device 30, for example such a 3CCD video camera, and the image evaluation computer 13 necessitates a conversion of the color signal produced by the image recording device 30 in the form of an analog voltage signal into a digital value that can be processed by the computer 13. This can be performed, for example, via a so called framegrabber or firewire, known per se. These devices can also be integrated in the image recording device 30 such that the latter can be connected directly to the computer 13.

The image recording device 30 is fastened on an adjustable frame 34, and it is inclined with its optical axis 54 in its vertical alignment by a variable acute angle α of preferably 5 degrees of angle with reference to the perpendicularly arranged container 20. The cylindrical container 20 and/or the body fluid 21 located therein can be recorded with comparatively few optical reflections with the aid of this measure.

Here, the optical axis 54 of the image recording device 30 runs in a vertical plane that lies perpendicular to the line A, the line B lying in this vertical plane.

Arranged above and in the middle relative to the analysis position 22 is a lifting rotary gripper 35 whose hydraulic drive is controlled by the control computer 12. The lifting rotary gripper 35 grips a container 20 located in the rack 18 and lifts it into the analysis position 22 and lowers it back into the rack 18 after recording by the image recording device 30.

During a recording by the image recording device, an antireflection plate 36 that can be moved to and fro horizontally lies on the side averted from said device, in order during recording to mask out the characters, such as a bar code, for example, printed on the label.

Before an analyzed container 20 is lowered by the lifting rotary gripper 35, the antireflection plate 36 is moved away on guide bolts 44 from the container 20 in order to make room for the lifting rotary gripper 35.

A plan view of the antireflection plate 36 is illustrated in FIG. 8. It is provided with a white, preferably dirt-repellant surface that is turned toward the container 20 and in which there is recessed a concave depression 37 adapted to the outer shape of the container 20. This depression 37 merges into flat surfaces 40 and 41 on both sides via rounded-off portions 38 and 39. The flat surfaces end in vertically arranged sharp edges 42 and 43 that serve as measuring edges. 15 to 50%, preferably 20 to 25% of the container 20 can be covered by the antireflection plate 36, such that labels of different size and shape can be masked out reliably.

Figure 6:
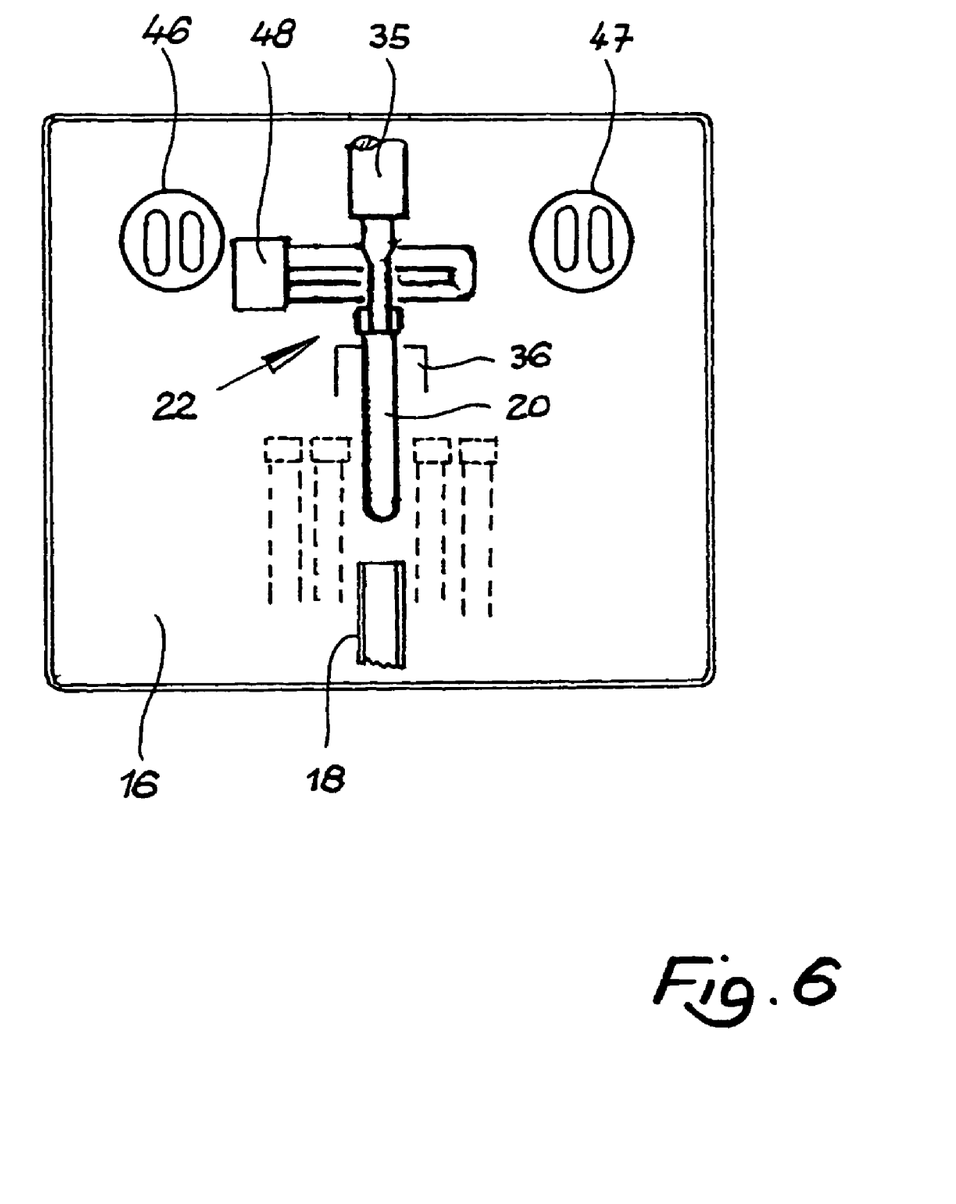
FIG. 6 shows the arrangement in accordance with FIG. 5 in the direction of view S, in a schematic illustration that is not true to scale.
Figure 9:
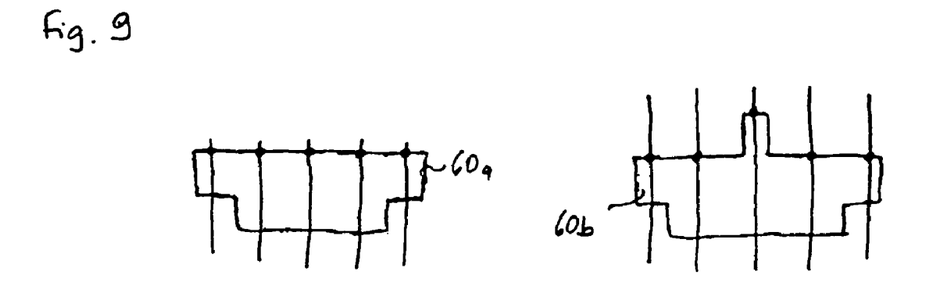
FIG. 9 shows top and bottom views of the antireflection plate.
Figure 10:
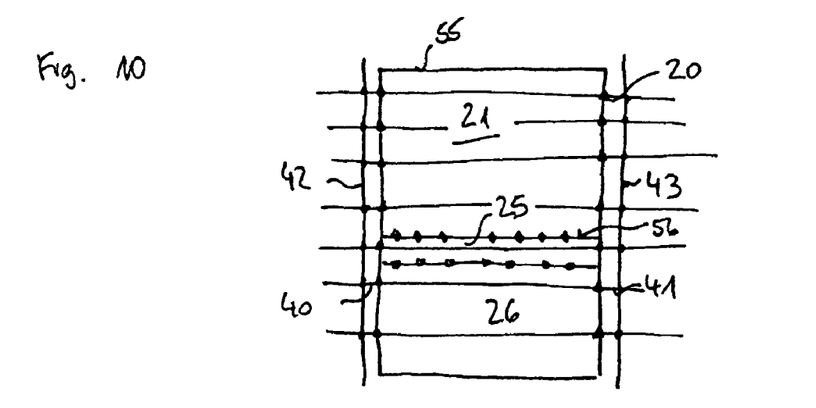
FIG. 10 shows a front view of a test tube positioned against the antireflection plate.

Finally, provided in the chamber 16, which has few, and if possible no optical reflections, is an illuminating device 45 that, during the process of analyzing a container 20 filled with body fluid, illuminates with as few reflections as possible said container, and the body fluid 21 contained therein.

An extensive empirical determination has shown that the arrangement of lamps described below results in an illumination that has comparatively few reflections.

The illuminating device 45 is arranged above a container 20 located in the analysis position 22, and comprises three lamps 46, 47 and 48.

In this case, arranged in each case on both sides of the container 20 located in the analysis position 22 is a lateral lamp 46 and 47, the arrangement being such that the mid points 49 and 50 of the two lamps 46 and 47 and the mid point 51 of the container 20 lie on a straight line A, and that a further, middle lamp 48 is provided in such a way that the mid points 53 and 51 of this middle lamp 48 and of the container 20 likewise lie on a straight line B, which runs perpendicular to the line A.

In addition, the three lamps 46, 47 and 48 have the same horizontal spacing from the container 22 located in the analysis position, which is sixty millimeters in the exemplary embodiment, for example. Furthermore, the vertical height of the lateral lamps 46 and 47 arranged on both sides of the container 20 located in the analysis position 22 is of greater dimension than the vertical height of the middle lamp 48. This difference is sixteen millimeters in the exemplary embodiment.

The mode of operation of the arrangement according to the invention is as follows:

Once a rack 18 filled with containers 20 has reached the analysis position with its first container 20, the image recording device 30 is used to determine the shape of the cap 24 sealing the container 20, and thus to determine the manufacturer and the dimensions of the container 20.

Then the lifting rotary gripper 45 lifts the container 20 on the basis of the dimensions determined into the suitable analysis position 22, rotates the container on the basis of the end edges 28 of the label 27 determined by the scanner 29 into a position ready for recording in which the window 52 is turned toward the image recording device 30. At the same time as the image recording device 30 is making one or more recordings of the body fluid 21, the shape of the cap 24 of the subsequent container is detected. The container 20 with the analyzed body fluid 21 is lowered again into the rack 18, the rack 18 is conveyed up to the subsequent container 20, and the latter is then gripped by the lifting rotary gripper 45 at the cap 24, moved into the analysis position 22 and aligned ready for recording.

In order to determine the quantity of the body fluid 21 located in the container 20, the image recording device 30 is used to determine the separating surface 55 between the surface of the body fluid 21 and air, and the separating surface 56 between the body fluid 21 and the separating means 25. Subsequently, the quantity of the body fluid located in the container 20 is calculated taking account of the diameter of the container by means of the image processing software on the basis of the data obtained.

The invention claimed is:

1. An arrangement for analyzing body fluids comprising:
   an image recording device;
   an image evaluation computer;
   a container;
   a chamber;
   an antireflection plate; and
   an illuminating device;
   wherein the image recording device being connected to the image evaluation computer, wherein the body fluid is provided in the container, the container and the antireflection plate being inside the chamber, the chamber having inner surfaces with matte black surfaces to minimize any optical reflections inside the chamber, the image recording device serving to produce at least one image of the body fluid in the container and being aligned with and focused on one side of the container, which is in a stationary analysis position, the illuminating device being arranged above the container, wherein the illuminating device serves to illuminate the container, the illuminating device comprising on opposite sides of the container located in the stationary analysis position a lateral lamp, the lateral lamps being arranged such that the mid points of the two lateral lamps and the mid point of the container lie on a straight line (A), the illuminating device further comprising a middle lamp being provided and arranged such that the mid points of this middle lamp and of the container likewise lie on a straight line (B), which runs perpendicular to the straight line (A), and the antireflection plate is arranged and provided on the side of the container opposite the image recording device, the antireflection plate is provided with a white surface to mask out characters on the container during imaging of the body fluid, and has a concave depression corresponding to the peripheral shape of the container.

2. The arrangement as claimed in claim 1, characterized in that the image recording device is a photographic still camera, a color image camera, a video camera or a spectral camera.

3. The arrangement as claimed in claim 1, characterized in that the chamber is a chamber with no optical reflections.

4. The arrangement as claimed in claim 1, characterized in that in its vertical alignment, the image recording device is aligned with and focused on the container at an acute angle.

5. The arrangement as claimed in claim 1, characterized in that the optical axis of the image recording device runs in a vertical plane that is perpendicular the line (A), the line (B) lying in this vertical plane.

6. The arrangement as claimed in claim 1, characterized in that the lamps have the same horizontal spacing from the container.

7. The arrangement as claimed in claim 6, characterized in that the spacing of each lamp from the container is sixty millimeters.

8. The arrangement as claimed in claim 1, characterized in that the vertical height of the lateral lamps arranged on two sides of the container located in the analysis position is of greater dimension than the vertical height of the middle lamp.

9. The arrangement as claimed in claim 8, characterized in that the difference in height between the lateral lamps and the middle lamp is sixteen millimeters.

10. The arrangement as claimed in claim 1, characterized in that a scanner is provided that is aligned with the container located in the analysis position.

11. The arrangement as claimed in claim 10, characterized in that the scanner is a bar code scanner.

12. The arrangement as claimed in claim 1, characterized in that the antireflection plate is arranged such that it can be moved away from the container from a position bearing against the container in the direction to the optical axis of the image recording device, and such that it can be moved up to the container again.

13. The arrangement as claimed in claim 1, characterized in that a handling apparatus is provided for moving a container from its transport position into its analysis position.

14. The arrangement as claimed in claim 13, characterized in that the handling apparatus comprises a lifting rotary gripper.

* * * * *